United States Patent
Mosticone et al.

(10) Patent No.: US 9,169,508 B2
(45) Date of Patent: Oct. 27, 2015

(54) METHOD FOR REAL-TIME DETECTION OF MICROORGANISMS IN A LIQUID CULTURE MEDIUM USING CELLULAR LYSIS

(75) Inventors: David Mosticone, Sainte-Consorce (FR); Jean-Claude Raymond, Bessenay (FR); Thierry Sofia, Saint-Genis-les-Ollieres (FR); Antoine Vimont, Lyons (FR)

(73) Assignee: bioMérieux, Marcy l'Etoile (FR)

( * ) Notice: Subject to any disclaimer, the term of this patent is extended or adjusted under 35 U.S.C. 154(b) by 398 days.

(21) Appl. No.: 12/918,195

(22) PCT Filed: Mar. 12, 2009

(86) PCT No.: PCT/FR2009/050413
§ 371 (c)(1),
(2), (4) Date: Aug. 18, 2010

(87) PCT Pub. No.: WO2009/122067
PCT Pub. Date: Oct. 8, 2009

(65) Prior Publication Data
US 2010/0331211 A1 Dec. 30, 2010

(30) Foreign Application Priority Data
Mar. 14, 2008 (FR) ...................................... 08 51654

(51) Int. Cl.
*C12Q 1/00* (2006.01)
*C12Q 1/04* (2006.01)
*C12Q 1/22* (2006.01)

(52) U.S. Cl.
CPC .. *C12Q 1/04* (2013.01); *C12Q 1/22* (2013.01); *C12Q 2304/00* (2013.01)

(58) Field of Classification Search
CPC ....................................................... C12Q 1/04
See application file for complete search history.

(56) References Cited

U.S. PATENT DOCUMENTS

| | | | |
|---|---|---|---|
| 4,659,658 A | | 4/1987 | McCarthy et al. |
| 2002/0086278 A1* | | 7/2002 | Gosnell et al. .................... 435/4 |
| 2007/0020719 A1* | | 1/2007 | Duran Vila et al. ............. 435/34 |

FOREIGN PATENT DOCUMENTS

| EP | 0 701 624 B1 | 8/1997 |
|---|---|---|
| EP | 1 199 567 B1 | 8/2006 |

OTHER PUBLICATIONS

Hansen et al., (J Clin Microbiol. Apr. 2003; 41(4): 1399-1403).*
Shih et al., J of Clin. Micro. vol. 6. No. 3:249-256.*
Gasanov et al., "Methods for the isolation and identification of *Listeria* spp. and *Listeria monocytogenes*: a review," FEMS Microbiology Reviews, 2005, pp. 851-875, vol. 29-No. 5.
Blanco et al., "A technique for the direct identification of haemolytic-pathogenic *listeria* on selective plating media," Letters in Applied Biology, 1989, pp. 125-128, vol. 9-No. 4 (XP-002500554).
"Microbiology of food an animal feeding stuffs—Horizontal method for the detection and enumeration of *Listeria monocytogenes*—Part 1: Detection method," British Standards, 1997, pp. 1-24 (XP-002500555).
Morel et al., "Transfusion-transmitted bacterial infection: residual risk and perspectives of prevention," Transfusion Clinique et Biologique, 2003, pp. 192-200, vol. 10-No. 3 (XP-002500556).
International Search Report mailed on Sep. 14, 2009 issued in International Patent Application No. PCT/FR2009/050413 (with translation).
International Preliminary Report on Patentability dated Nov. 2, 2010 issued in International Patent Application No. PCT/FR2009/050413 (with translation).

* cited by examiner

*Primary Examiner* — Albert Navarro
(74) *Attorney, Agent, or Firm* — Oliff PLC

(57) ABSTRACT

The present invention relates to a method for detecting at least one target microorganism that may be present in a sample, comprising the steps of:
- a) bringing into contact, in a container: said sample, a medium that enables the growth of the target microorganism(s), and a cell population capable of being lysed by the target microorganism(s);
- b) subjecting the whole to a temperature that promotes the growth of the target microorganism(s); and
- c) observing, in real time, lysis of the cell population indicating the presence of the target microorganism(s).

The present invention also relates to a method for detecting and identifying at least one target microorganism that may be present in a sample.

26 Claims, No Drawings

METHOD FOR REAL-TIME DETECTION OF MICROORGANISMS IN A LIQUID CULTURE MEDIUM USING CELLULAR LYSIS

CROSS-REFERENCE TO RELATED APPLICATIONS

This application claims priority to FR 0851654 filed in France on Mar. 14, 2008, is a national phase entry of PCT/FR2009/050413 filed on Mar. 12, 2009 and the entire disclosures of which are hereby incorporated by reference in their entirety.

The field of the invention is that of clinical or industrial microbiological testing. More particularly, it involves a method for identifying one or more microorganisms by means of a cell lysis reaction carried out simultaneously with the enrichment of the sample in microorganisms.

Microbiological analysis requires precise techniques in which the time for obtaining the result should be as short as possible.

In the medical field, it is necessary to predict and diagnose the risk of infection: the faster and more precise the diagnosis, the more effective is the treatment of the patients and the more the risk of transmission is minimized. The approach is similar for animal health.

In the food-processing fields, the specifications are identical. These specifications distinguish, however, between pathogenic microorganisms and their toxins, the investigation of which applies to marketed products, nonpathogenic microorganisms, used as quality indicators for the production process, from the raw products to the final products, all along the chain, and bacteria of technological interest such as ferments. The rapid and precise detection of presumed contaminants makes it possible to test for them and to thus initiate corrective actions.

Technically, the microbiological analysis can implement one or more phases of pre-enrichment/enrichment, one or more phases of detection, one or more phases of counting of the microorganisms. For specific applications such as food-processing microbiological testing, a confirmation phase may also be required, in order to comply with the standards in force in this field.

The pre-enrichment/enrichment phase calls for selective or nonselective culture media well-known to those skilled in the art. Ready-to-use culture media, often in liquid form, based on formulations of conventional media are commercially available.

The detection phase is based on demonstrating the metabolic characteristics of the microorganisms being sought. Specific enzyme substrates are conventionally used. These enzyme substrates are generally composed of two parts, a first part specific for the enzyme activity to be revealed, also called target part, and a second part which acts as a label, also called label part, generally constituted of a chromophore or a fluorophore. Through the choice of these substrates, depending on whether or not there is a reaction, it is possible to characterize the nature of a microorganism or to distinguish various groups of microorganisms. Thus, the appearance or the disappearance of a coloration or of a fluorescence will be the signature of a microorganism genus or type. In this regard, the use of chromogenic media enables the simultaneous detection and identification of the microorganisms being sought. It simplifies the process and substantially reduces the time for obtaining the result. By way of concrete example, mention will be made of the applicant's ChromID® media. These chromogenic media are based on the detection of metabolic characteristics specific for the microorganisms being sought, for instance the beta-glucuronidase enzyme activity for *Escherichia coli*. However, some microorganisms, or some subtypes, for instance *Escherichia coli* O157:H7, do not exhibit any specific enzyme activity and cannot therefore be detected using a chromogenic culture medium.

The confirmation phase, for its part, is more particularly linked to microbiological analysis in the food-processing field. Specifically, when the result of the previously developed methods is positive, it is necessary to confirm the presence of the pathogen being sought. This means that an additional test and the use of a principle of detection that is different than that used in the first analysis are required. Molecular biology techniques, based on the genomic characteristics of the microorganisms being sought, constitute one of the means used to confirm the identification. By way of example, mention will be made of conventional amplification techniques such as PCR (Polymerase Chain Reaction) and NASBA (Nucleic Acid Sequence Based Amplification), which can be coupled with real-time detection techniques known to those skilled in the art.

Immunoassays constitute another of the technologies used for the confirmation test. They make use of the immunogenic characteristics of the microorganisms being sought. Mention may be made, nonexhaustively, of the competition or sandwich ELISA (Enzyme Linked ImmunoSorbent Assay) techniques or the immunoagglutination techniques, detecting epitopes of the microorganisms being sought. The latter make use of functionalized solid supports, such as beads (for example, latex particles), coated with monoclonal or polyclonal antibodies, said functionalized supports being brought into contact with a biological sample, as indicated, for example, in the granted European patents EP 0 701 624 and EP 1 199 567. Alternatively, as described in U.S. Pat. No. 4,659,658, the solid particles can be coated with lectins which bind specifically to sugars located at the surface of a given microorganism. In any event, the appearance of the agglutination makes it possible to definitely identify the microorganism being sought.

The complete and precise identification of a microorganism in a sample therefore requires the sequence of several steps: enrichment, detection, confirmation. The standardization of routinely used tests has enabled the automation of the detection methods, which remain, however, slow to carry out. One drawback of the prior art is in fact that these steps are carried out sequentially. Another drawback is that the specific interaction reaction used for the confirmation step, which is an immunological reaction or a molecular hybridization reaction, is most commonly read at "end point". During this time, in the food-processing industry, the entire batch of final product is blocked while awaiting the result of the confirmation, and in clinical terms, the setting up of the relative antibiotic treatment and the preventive measures is delayed.

In view of the prior art considered, a method which combines the steps of enrichment, detection and precise identification is therefore lacking. Concretely, such a method would bring together rapidity, specificity and sensitivity.

The present invention therefore proposes to overcome the drawbacks described above by simultaneously using a culture of microorganisms and at least one reaction of cell lysis by said microorganisms, in a liquid medium.

More specifically, the invention relates, firstly, to a method for detecting and identifying at least one target microorganism that may be present in a sample, comprising the steps of:

a) bringing into contact, in a container: a culture medium that enables the growth and/or detection of the target microorganism(s), said sample and a cell population capable of being lysed by the target microorganism(s);

b) subjecting the whole to a temperature that promotes the growth and/or detection of the target microorganism(s);
c) observing, in real time, lysis of the cell population indicating the presence of the target microorganism(s) or confirming said presence when said target microorganisms are detected when step b) has been completed.

Another subject of the invention relates to a method for detecting and identifying at least one target microorganism that may be present in a sample, comprising the steps of:
a) bringing into contact, in a container: a culture medium that enables the growth and/or identification of the target microorganism(s), said sample and a cell population capable of being lysed by the target microorganism(s);
b) subjecting the whole to a temperature that promotes the growth and/or identification of the target microorganism(s); and
c) observing, in real time, lysis of the cell population making it possible to identify the target microorganism(s) or to confirm said identification, when said target microorganism(s) is (are) identified in said culture medium, when step b) has been completed.

Another subject of the present invention relates to a method for detecting and identifying at least one target microorganism that may be present in a sample, comprising the steps of:
a) bringing into contact, in a container: a culture medium that enables the growth and identification of the target microorganism(s), said sample and a cell population capable of being lysed by the target microorganism(s);
b) subjecting the whole to a temperature that promotes the growth and identification of microorganisms; and
c) observing, in real time, lysis of the cell population making it possible to supplement the identification of the microorganism(s), made when step b) has been completed.

The expression "supplement the identification" is intended to mean provide additional information making it possible to specify the identification of the target microorganism(s). For example, in step a), the culture medium used may be specific for bacteria of the *Escherichia coli* genus and may comprise a substrate specific for this bacterial genus, such that the presence of such bacteria in the test sample is characterized by a modification of the culture medium, such as a change in color, if the substrate used is a chromogenic substrate. The lysis of the cell population (Vero cells for example) taking place in step c) may, for example, make it possible to demonstrate a particular strain of the *Escherichia coli* genus, such as *E. coli* O157:H7, which is an enteropathogenic strain.

The term "cell population" is intended to mean any type of cell or vesicle, of natural origin or derived from chemical or biological engineering, capable of being lysed specifically or nonspecifically by the target microorganism(s). One type of cell that can be used in the methods according to the invention is, for example, erythrocytes or red blood cells. Specifically, these cells are lysed by hemolytic bacteria, in particular β-hemolytic bacteria, such as certain strains of *Streptococcus* and *Listeria*. The red blood cells used are capable of containing detection-assisting compounds, such as chromophore or fluorophore compounds, which are released when the red blood cells are lysed. A technology for encapsulating compounds in red blood cells has been developed by the company ERYtech Pharma®.

It is also possible to envisage the use of lipid vesicles of which the membrane can be specifically or nonspecifically lysed by a type of microorganism. This is the case, for example, with liposomes.

The temperature that promotes the growth of microorganisms is between 20 and 44° C. and the sample is kept at this temperature for a period of time sufficient to enable the detection of microorganisms, i.e. a period of between 6 and 96 hours.

The combined use of these various techniques, in a single container, makes it possible both to save time and to limit handling, and therefore contamination of the handlers or of the samples, leading in the latter case to false-positives. In addition, the implementation of the invention can be automated. It will also be noted that the time saved is linked both to the combining of two steps into a single step and to the detection of the cell lysis in real time.

Advantageously, steps a) and c) of the methods described above use chromogenic compounds (also called chromophores) or fluorescent compounds (also called fluorophores).

More particularly, in the two methods of detection and identification, detection can preferably use the appearance or disappearance of a coloration or of a fluorescence. Moreover, in all the methods which are subjects of the invention, cell lysis can advantageously be demonstrated by the appearance or the disappearance of a coloration or of a fluorescence.

Thus, according to one particular embodiment of the invention, the cell lysis consists of hemolysis, namely the lysis of red blood cells. Such an embodiment is particularly advantageous when seeking to demonstrate hemolytic bacteria. In the present case, the hemolysis reaction will be demonstrated through a disappearance of the fluorescence. This is because it is found that, when red blood cells are lysed, the hemoglobin contained in the latter is released into the culture medium. It then masks the fluorescence emitted by the fluorogenic compounds contained in the culture medium.

Preferably, the container is taken from the group constituted of microplates, microcupules, microtubes, capillaries or multiwell cards.

Advantageously, the method which is the subject of the invention can also comprise a step of counting the microorganisms, preferably according to the most probable number method explained in patent EP 1 105 457 by the applicant.

In addition, a subject of the invention is a diagnostic kit for carrying out the method according to the various embodiments developed above. The kit comprises:
a container;
a selective or nonselective culture medium, said culture medium optionally containing a substrate specific for the metabolism of the microbial genus or species to be detected; and
a cell population capable of being lysed by the target microorganism(s).

Advantageously, the container is taken from the group constituted of microplates, microcupules, microtubes, capillaries or multiwell cards.

According to a first preferred embodiment, the cell population consists of red blood cells.

According to a second preferred embodiment, the cell population consists of liposomes.

The diagnostic kit according to the invention may also comprise at least one chromogenic or fluorescent compound.

Finally, a last subject of the invention relates to the use of a diagnostic kit according to the invention, for detecting and/or identifying at least one microorganism that may be present in a sample.

The invention will be understood more clearly on reading the detailed description which follows and the nonlimiting examples given by way of illustration.

The method which is the subject of the invention can be used for samples of food, environmental or clinical origin. The sample is defined as a small part or small amount isolated from an entity for analysis.

Among the samples of food origin, mention may be made, nonexhaustively, of a sample of milk products (yogurts, cheeses, etc.), of meat, of fish, of eggs, of fruit, of vegetables, of water or of a drink (milk, fruit juice, soda, etc.). These samples of food origin may also come from prepared dishes or sauces. Finally, a food sample may be derived from an animal feed, such as, in particular, animal meals.

Mention will also be made of samples related to the environment, such as samples taken from a surface, from water or from the air.

The samples of clinical origin may correspond to biological fluid (whole blood, serum, plasma, urine, cerebrospinal fluid) samples taken, fecal samples taken, samples taken from the nose, the throat, the skin, wounds, organs, tissues or isolated cells, etc.

The microbiological testing corresponds to the analysis of a sample with the aim of isolating and/or identifying and/or counting the microorganisms potentially present, such as bacteria or yeast. Technically, this analysis comprises the growth, in vitro, of the microorganisms in a culture medium. The term "culture medium" is intended to mean a medium comprising all the components necessary for the survival and/or growth of microorganisms. The culture medium may contain optional additives such as, for example: peptones, one or more growth factors, carbohydrates, one or more selective agents, buffers, one or more gelling agents, etc. This culture medium may be in a liquid or gel form that is ready to use, i.e. ready for seeding in a tube or flask or on a Petri dish.

For the purpose of the present invention, the term "microorganism" covers Gram-positive or Gram-negative bacteria, yeasts, molds and, more generally, unicellular organisms, invisible to the naked eye, which can be handled and multiplied in the laboratory.

In general, the culture medium may in addition contain a substrate for detecting an enzyme activity or a metabolic activity of the target microorganisms by means of a directly or indirectly detectable signal. For direct detection, this substrate can be linked to a part which acts as a label, which may be fluorescent or chromogenic. For indirect detection, the culture medium according to the invention may in addition comprise a pH indicator, sensitive to the variation in pH induced by the consumption of the substrate and revealing the growth of the target microorganisms. Said pH indicator may be a chromophore or a fluorophore. As examples of chromophores, mention will be made of neutral red, aniline blue and bromocresol blue. The fluorophores comprise, for example, 4-methylumbelliferone, aminocoumarin derivatives and resorufin derivatives.

For the purpose of the present invention, the identification of the microorganism being sought, potentially carried out by searching for its metabolic characteristics, should be confirmed. This confirmation can make use of cell lysis reactions.

The term "cell lysis" is intended to mean the result of a direct or indirect action of the microorganisms on cells or vesicles, of natural or unnatural origin, leading to lysis of said cells or destruction of said vesicles. The presence, in the sample, of hemolytic bacteria, such as β-hemolytic streptococci, can be detected by lysis of the red blood cells contained in the culture medium.

The cell lysis can be detected visually, or by means of an automatic optical reader according to various principles known to those skilled in the art, among which mention will be made, nonexhaustively, of:

(1) the detection of the appearance of a fluorescence, by release of fluorophores during the lysis, said fluorophores being initially contained in the cells or vesicles in suspension in the culture medium; and (2) the disappearance of the fluorescence in the medium, due to masking thereof by the hemoglobin released by lysis of the red blood cells initially in suspension in the culture medium;

(3) the disappearance of the fluorescence in the medium, due to masking thereof by a compound released during the lysis, said compound being initially contained in the cells or vesicles in suspension in the culture medium;

(3) the detection of a change in or an appearance of color owing to the release, during the lysis, of chromophores initially contained in the cells or vesicles, initially in suspension in the culture medium;

(4) the detection of a change in color of the culture medium due to the release of hemoglobin owing to lysis of the red blood cells initially in suspension in the culture medium.

The fluorophores that can be used were mentioned above and comprise 4-methylumbelliferone, aminocoumarin derivatives or resorufin derivatives.

The chromophores that can be used are those conventionally used in chromogenic culture media and well known to those skilled in the art.

The fluorescence-masking compounds that can be used are, for example, paranitrophenol or hemoglobin.

The operations of culturing/identification and then cell lysis at end point, described in two steps, are, according to the present invention, combined in a single step, the cell lysis being detected in real time. By way of illustration, mention will be made of the possible identification, in a sample of food origin, of *Listeria monocytogenes*: the detection of *Listeria monocytogenes* can be carried out using a culture medium which is selective for this bacterium and the confirmation of the presence of *Listeria monocytogenes* will be carried out simultaneously by means of the cell lysis reaction, detected in real time. This lysis reaction will be obtained, for example, by using synthetic vesicles, of the liposome type, carrying, at their surface, motifs specifically recognized by the hemolysin produced by *Listeria monocytogenes*, thus leading to the lysis of said vesicles.

In one particular embodiment, the invention can be carried out in containers such as microplates, microcupules, microtubes, capillaries, etc.

Advantageously, the method according to the invention can be combined with an automatic microbiological testing device of TEMPO® type, as developed by the applicant, and can optionally enable counting of the detected microorganisms.

The method, which is the subject of the invention, can be carried out using a kit comprising: a reaction medium containing a nutritive base, sensitized particles and, optionally, a chromogenic substrate specific for the microorganism(s) being sought. Said medium is resuspended with an aliquot of the sample to be analyzed. Advantageously, the kit for carrying out the method according to the invention can also contain a solid container of microplate, microtube, microcupule, capillary, VITEK® card or TEMPO® card type.

EXAMPLE

Counting of *Listeria ivanovii* Based on the Use of Red Blood Cells of Animal Origin The test consists here in counting *Listeria ivanovii* bacteria biochemically using the TEMPO® system, marketed by the applicant. This test is based on masking of fluorescence after specific lysis of red blood cells (release of hemoglobin) by *Listeria ivanovii*, derived from a pure strain (ref. ATCC 70408), initially present in one or more wells of the card.

Protocol:

Step 1: Resuspension of the Reaction Medium with an Aliquot of the Sample to be Analyzed:

The reaction medium contains:
red blood cells of animal origin (sheep, horse);
a fluorescent label (e.g. 7-aminomethylcoumarin (7-AMC), 4-methylumbelliferone (4-MU));
a nutritive base: buffered peptone water (bioMérieux reference 51094).

A bacterial suspension of *Listeria ivanovii* (1000 CFU/ml) is obtained from a sample of pure strain.

4 ml of reaction medium are inoculated with an aliquot of 40 μl of the bacterial suspension, which corresponds to a dilution to $1/100^{th}$ of the bacterial suspension. The reaction medium is then introduced into a TEMPO® card, in accordance with the protocol in force, with a view to performing a count.

Step 2: Incubation of the Card:

The TEMPO cards are then incubated at 37° C. for 16 to 24 h. During this incubation period, the reaction of red blood cell lysis due to the production of listeriolysins (hemolysins produced by *Listeria ivanovii*) takes place simultaneously with the bacterial growth, in the event of target cells being present in the well(s) under consideration.

Step 3: Reading of the Test after 24 h of Incubation:

After incubation, the presence of *Listeria ivanovii*, in one or more wells of the card, will induce specific lysis of the red blood cells, thus generating release of hemoglobin and therefore masking of the fluorescence in the wells concerned, which are then defined as positive.

The number of positive wells is then counted in order to determine, via the MPN table, a number of colony forming units (CFU) of *Listeria ivanovii* per gram or milliliter of sample.

TABLE 1

| Relative fluorescence units (RFU) in each type of well of the TEMPO card | |
|---|---|
| Type of well | Number of positive wells |
| Large | 12 |
| Medium | 8 |
| Small | 1 |

On the basis of the number of positive wells obtained, the concentration of bacteria in the suspension introduced into the card is determined using the Most Probable Number (MPN) method. This calculation is carried out by means of the algorithm loaded in the TEMPO® instrument. The value obtained is 10 CFU/ml. Given that the bacterial suspension had been diluted to $1/100^{th}$ in the reaction medium, the starting concentration of the latter is determined, and is 1000 CFU/ml.

The invention claimed is:

1. A method for detecting or identifying at least one target microorganism in a sample if present in the sample, comprising:

forming a liquid mixture from at least (i) the sample, (ii) a liquid culture medium that enables the growth of the target microorganism, and (iii) a population of cells or vesicles capable of being lysed by the target microorganism;

subjecting the liquid mixture to a temperature that promotes growth of the target microorganism in order to culture the target microorganism if present in the sample; and determining whether the cells or vesicles have been lysed, wherein lysis of the cells or vesicles indicates a positive detection or identification of the target microorganism in the sample.

2. The method of claim 1, wherein the method is performed with the liquid mixture in a single container selected from the group consisting of microplates, microcupules, microtubes, capillaries, and multiwell cards.

3. The method of claim 1, wherein the liquid mixture is subjected to a temperature from 20° C. to 44° C. for a time period of 6 to 96 hours to promote growth of the target microorganism in order to culture the target microorganism if present in the sample.

4. The method of claim 1, further comprising counting the target microorganism if detected or identified in the sample.

5. The method of claim 1, wherein the cells or vesicles are biologically and/or chemically engineered cells or vesicles.

6. The method of claim 1, wherein the cells or vesicles are red blood cells.

7. The method of claim 1, wherein the cells or vesicles are lipid vesicles.

8. The method of claim 1, wherein lysis of the cells or vesicles is determined by detecting the appearance or disappearance of coloration or fluorescence in the liquid mixture.

9. The method of claim 1, wherein the cells or vesicles are red blood cells, and lysis of the red blood cells is determined by detecting that there is a color change in the liquid mixture due to release of hemoglobin from lysed red blood cells.

10. The method of claim 1, wherein the cells or vesicles initially contain a fluorophore or chromophore, and lysis of the cells or vesicles is determined by detecting that the fluorophore or chromophore is released from the cells or vesicles due to lysis.

11. The method of claim 10, wherein the cells or vesicles are red blood cells that have been modified to contain the fluorophore or chromophore.

12. The method of claim 1, wherein the liquid mixture further comprises a fluorophore and the cells or vesicles initially contain a fluorescence-masking compound, and lysis of the cells or vesicles is determined by detecting that there is masking of the fluorophore by release of the fluorescence-masking compound from the cells or vesicles due to lysis.

13. The method of claim 12, wherein the cells or vesicles are red blood cells, and the fluorescence-masking compound is hemoglobin.

14. A method for detecting or identifying at least one target microorganism in a sample if present in the sample, comprising:

forming a liquid mixture from at least (i) the sample, (ii) a liquid culture medium that enables the growth of the target microorganism, (iii) a substrate for directly or indirectly detecting an enzymatic or metabolic activity of the target microorganism, and (iv) a population of cells or vesicles capable of being lysed by the target microorganism;

subjecting the liquid mixture to a temperature that promotes growth of the target microorganism in order to culture the target microorganism if present in the sample;

detecting whether a detectable signal indicative of a positive detection or identification of the target microorganism is present due to the enzymatic or metabolic activity of the target microorganism acting on the substrate; and determining whether the cells or vesicles have been lysed, wherein lysis of the cells or vesicles indicates confirmation of a positive detection or identification of the target microorganism or supplements a positive identification of the target microorganism in the sample.

15. The method of claim 14, wherein the substrate is a chromogenic substrate, and the detectable signal is a color change.

16. The method of claim 14, wherein the substrate is a fluorogenic substrate, and the detectable signal is a fluorescent signal emitted upon excitation.

17. The method of claim 14, wherein the substrate is a pH indicator.

18. The method of claim 14, wherein lysis of the cells or vesicles is determined by detecting the appearance or disappearance of coloration or fluorescence in the liquid mixture.

19. The method of claim 14, wherein the cells or vesicles initially contain a fluorophore or chromophore, and lysis of the cells or vesicles is determined by detecting that the fluorophore or chromophore is released from the cells or vesicles due to lysis.

20. The method of claim 14, wherein the liquid mixture further comprises a fluorophore and the cells or vesicles initially contain a fluorescence-masking compound, and lysis of the cells or vesicles is determined by detecting that there is masking of the fluorophore by release of the fluorescence-masking compound from the cells or vesicles due to lysis.

21. The method of claim 20, wherein the cells or vesicles are red blood cells, and the fluorescence-masking compound is hemoglobin.

22. A diagnostic kit including one or more containers, the kit comprising:
   a selective or nonselective liquid culture medium for enabling the growth of at least one target microorganism;
   optionally a substrate, provided in the liquid culture medium, for directly or indirectly detecting an enzymatic or metabolic activity of the target microorganism; and
   a population of cells or vesicles capable of being lysed by the target microorganism,
   wherein:
      the culture medium comprises a fluorophore; or
      the population of cells or vesicles comprises a fluorophore or a chromophore.

23. The diagnostic kit of claim 22, wherein the substrate is provided in the liquid culture medium.

24. The diagnostic kit of claim 22, wherein the population of cells or vesicles is provided in the liquid culture medium.

25. The diagnostic kit of claim 22, wherein the culture medium comprises peptones.

26. The diagnostic kit of claim 22, wherein the culture medium comprises a pH indicator.

* * * * *